United States Patent
Knebel et al.

(10) Patent No.: US 9,340,484 B2
(45) Date of Patent: May 17, 2016

(54) METHOD FOR PRODUCING BICYCLIC OR TRICYCLIC (METH)ACRYLATES

(71) Applicants: Joachim Knebel, Alsbach-Haehnlein (DE); Thorben Schuetz, Alsbach-Haehnlein (DE); Guenther Graeff, Alsbach-Haehnlein (DE); Hedwig Luise Johanna Ohl, Darmstadt (DE)

(72) Inventors: Joachim Knebel, Alsbach-Haehnlein (DE); Thorben Schuetz, Alsbach-Haehnlein (DE); Guenther Graeff, Alsbach-Haehnlein (DE); Thomas Ohl

(73) Assignee: EVONIK ROEHM GmbH, Darmstadt (DE)

( * ) Notice: Subject to any disclaimer, the term of this patent is extended or adjusted under 35 U.S.C. 154(b) by 31 days.

(21) Appl. No.: 14/351,667

(22) PCT Filed: Nov. 20, 2012

(86) PCT No.: PCT/EP2012/073087
§ 371 (c)(1),
(2) Date: Apr. 14, 2014

(87) PCT Pub. No.: WO2013/092072
PCT Pub. Date: Jun. 27, 2013

(65) Prior Publication Data
US 2014/0235889 A1    Aug. 21, 2014

(30) Foreign Application Priority Data

Dec. 22, 2011    (DE) .......................... 10 2011 089 504

(51) Int. Cl.
*C07C 69/52*    (2006.01)
*C07C 67/04*    (2006.01)

(52) U.S. Cl.
CPC ............. *C07C 67/04* (2013.01); *C07C 2102/42* (2013.01); *C07C 2103/68* (2013.01)

(58) Field of Classification Search
CPC ....................................................... C07C 69/52
USPC ........................................................ 560/220
See application file for complete search history.

(56) References Cited

U.S. PATENT DOCUMENTS

| 5,596,127 | A  | 1/1997  | Gscheidmeier et al. |
|-----------|----|---------|---------------------|
| 2009/0299009 | A1 | 12/2009 | Yonehara |
| 2012/0232222 | A1 | 9/2012  | Schütz et al. |
| 2014/0045993 | A1 | 2/2014  | Koemmelt et al. |

FOREIGN PATENT DOCUMENTS

| DE | 44 19 686   | 12/1995 |
|----|-------------|---------|
| WO | 2008 023823 | 2/2008  |

OTHER PUBLICATIONS

Heidekum, Journal of catalysis, Academic Press, vol. 181, No. 2, pp. 217-222, 1999.*
Heidekum, et al. "Addition of Carboxylic Acids to Cyclic Olefins Catalyzed by Strong Acidic Ion-Exchange Resins", Journal of catalysis, Academic Press, vol. 181, No. 2, pp. 217-222, XP004443248, Jan. 25, 1999.
Adms, et al., "Methyl t-Butyl Ether (MTBE)Production; A Comparision of Montmorillonite-Derived Catalysts With an Ion-Exchange Resin", Clays and Clay Minerals, vol. 34, No. 5, pp. 597-603, (1986).
International Search Report Issued Jan. 14, 2013 in PCT/EP12/073087 Filed Dec. 11, 2012.
German Search Report Issued Dec. 22, 2011 in the Priority Application 10 2011 089504.3.

* cited by examiner

*Primary Examiner* — Yong Chu
*Assistant Examiner* — Sonya Wright
(74) *Attorney, Agent, or Firm* — Oblon, McClelland, Maier & Neustadt, L.L.P.

(57) ABSTRACT

Process for preparing bicyclic or tricyclic (meth)acrylates by reacting (meth)acrylic acid with a bicyclic or tricyclic hydrocarbon which contains at least one double bond using montmorillonite as catalyst.

5 Claims, No Drawings

METHOD FOR PRODUCING BICYCLIC OR TRICYCLIC (METH)ACRYLATES

The present invention relates to a process for preparing bicyclic or tricyclic (meth)acrylates by reacting (meth)acrylic acid with bicyclic or tricyclic hydrocarbons which bear at least one double bond.

The term (meth)acrylates refers to both derivatives of methacrylic and compounds of acrylic acid.

Processes for preparing bicyclic (meth)acrylates are known from the prior art. Thus, for example, EP 718271 describes the preparation of isobornyl (meth)acrylates from camphene and (meth)acrylic acid over acidic ion exchangers. EP 759423 claims a similar preparative process using zirconium sulphate as catalyst. Two processes employing homogeneous catalysis are described in DE 19920796 (carried out in the presence of sulphuric acid) and in DE 4316004 (carried out in the presence of molybdophosphoric acid). Furthermore, DE 19930721 discloses a transesterification process starting from isoborneol and MMA or ethyl acrylate for preparing isobornyl (meth)acrylate.

However, the processes mentioned have disadvantages. Firstly, catalyst (zirconium sulphate) or starting compound (isoborneol) are not commercially available. Secondly, thermal stability and life of the catalyst used (ion exchanger) are limited and lead to low molecular weight, colour-imparting decomposition products being discharged. Over its life, activity and selectivity decrease.

Complicated purification steps are necessary for separating off the resulting by-products (camphene oligomers).

It is therefore an object of the present invention to provide an alternative process for preparing bicyclic or tricyclic (meth)acrylates, which process completely or at least partly eliminates the disadvantages mentioned.

This object and further objects which are not described in detail but can readily be deduced or derived from the introductory presentation of the prior art are achieved by a process having the features of claim 1. Advantageous modifications of the process of the invention are protected in the claims referring back to claim 1.

The present invention provides a process for preparing bicyclic or tricyclic (meth)acrylates by reacting (meth)acrylic acid with a bicyclic or tricyclic hydrocarbon which contains at least one double bond, characterized in that montmorillonite is used as catalyst. As an inorganic material, montmorillonite has the advantage over the catalysts used in the prior art of higher thermal stability compared to the polystyrene-based cation exchangers, the absence of colour-imparting decomposition products and commercial availability. Furthermore, it can be removed from the reaction by means of a relatively simple filtration step and can surprisingly be used a number of times for the same reaction without disadvantages.

In principle, all bicyclic or tricyclic hydrocarbons which have at least one double bond can be reacted with (meth) acrylic acid in the process of the invention. Examples of bicyclic hydrocarbons which may be mentioned are pinene, camphene, fenchene, isobornylene, norbornene, isocamphene, thujene, sabinene, carene and santalene, and examples of tricyclic hydrocarbons are dicyclopentadiene, gurjunene, aristolone, cedrene and bourbonene and tricycloalkenes as can be prepared, for example, as described in U.S. Pat. No. 3,725,366 as starting compounds employed there. Preference is given to using camphene, norbornene or dicyclopentadiene.

Montmorillonite is used as catalyst. Montmorillonite, which gets it name from its deposit at Montmorillon in southern France, where the mineral was discovered for the first time in Europe, is a frequently occurring mineral from the group of clay minerals within the mineral class of silicates and germanates. It crystallizes in the monoclinic crystal system with the chemical composition $\sim(Al_{1.67}Mg_{0.33})[(OH)_2|Si_4O_{10}].Na_{0.33}(H_2O)_4$ and develops microscopically small, needle-like crystals which usually form compact, heavy aggregates. Montmorillonite has a high ion-exchange capacity since it can exchange the cations between the layers for the cations present in solution. On addition of water, the mineral expands to a multiple of the original size. The 9th edition of the Strunz mineral classification system which has been valid since 2001 and is used by the International Mineralogical Association (IMA) assigns montmorillonite to the class of sheet silicates (phyllosilicates). This class is further divided according to the crystal structure, so that the mineral is, corresponding to its structure, to be found in the subclass of sheet silicates (phyllosilicates) having mica platelets composed of tetrahedral or octahedral networks where it gives its name to the montmorillonite group having the system No. 9.EC.40. Further details on montmorillonite may be found in Hugo Strunz, Ernest H. Nickel: Strunz Mineralogical Tables, 9th Edition, E. Schweizerbart'sche Verlagsbuchhandlung (Nägele and Obermiller), Stuttgart 2001, ISBN 3-510-65188-X. In the process of the invention, a naturally occurring variant of montmorillonite named bentonite after its source in Benton, Wyo., USA is preferably used. Bentonite is the name for an industrial mineral which contains not only the main mineral montmorillonite but also accompanying minerals such as quartz, mica, feldspar, pyrite or lime. This product is commercially available under the name Montmorillonite K10 from Südchemie. The amounts of montmorillonite used in the reaction are in the range 5-50% by weight, preferably 10-40% by weight and particularly preferably 15-30% by weight, based on the amount of (meth)acrylic acid used.

In the process of the invention, a polymerizable compound is reacted. The reaction therefore has to be carried out in the presence of polymerization inhibitors. Preferred polymerization inhibitors include, inter alia, phenothiazine, tert-butylcatechol, hydroquinone monomethyl ether, hydroquinone, 4-hydroxy-2,2,6,6-tetra-methylpiperidineoxyl (TEMPOL) or mixtures thereof, with the effectiveness of these inhibitors sometimes being able to be improved by use of oxygen. The polymerization inhibitors can be used in a concentration in the range from 0.001 to 2.0% by weight, particularly preferably in the range from 0.01 to 0.2% by weight, based on (meth)acrylic acid.

The reaction can be carried out continuously or batchwise in plants with which a person skilled in the art would be familiar. Possible reactors are CSTRs or tube reactors, with preference being given to the reaction taking place in a CSTR. The catalyst is removed by means of conventional filtration steps and can optionally be reused for the reaction. In general, a distillation step to purify the product should follow.

The reaction according to the invention takes place under atmospheric pressure or slightly superatmospheric pressure, preferably in the range 1-10 bar, particularly preferably 1-5 bar. The reaction temperatures are in the range 50-250° C., preferably 70-200° C. and particularly preferably 90-160° C. The residence times in the batch mode are generally 5-30 h, preferably 5-20 h, particularly preferably 5-10 h. The subsequent optional distillation step to purify the product is guided by the composition of the reaction mixture of products and starting materials obtained and their boiling points and is carried out in an apparatus, generally at least one separation column, and by a procedure with which those skilled in the art will be familiar.

The (meth)acrylates obtained according to the invention can be used in a manner known per se as monomers in surface coating resins or radiation-curable coatings. The following examples illustrate the invention but do not restrict it in any way.

EXAMPLE 1

66.3 g (0.77 mol) of methacrylic acid, 95.4 g (0.70 mol) of camphene, 0.078 g of hydroquinone monomethyl ether as polymerization inhibitor and 16.9 g of montmorillonite K10 (SÜdchemie) are weighed into a 500 ml four-neck round-bottom flask containing a sickle stirrer with stirrer sleeve, thermometer, reflux condenser, air inlet tube and temperature-regulated oil bath. While stirring and passing in air, the mixture is heated at 90° C. for 6 hours. The mixture is allowed to cool, the montmorillonite is filtered off and the filtrate is analysed by gas chromatography. The catalyst is reused in the subsequent examples. GC analysis indicates 10.9% of unreacted methacrylic acid, 20.5% of unreacted camphene, 60.3% of isobornyl methacrylate and also 6.3% of camphene dimer and 0.6% isoborneol.

EXAMPLES 2-7

In Examples 2-7, Example 1 is in each case repeated using the catalyst from the preceding batch. The composition of the reaction mixtures obtained is shown in Tab. 1.

TABLE 1

| | | GC analysis (amounts in %) | | | | |
|---|---|---|---|---|---|---|
| Example | Repeat use of catalyst | Methacrylic acid | Camphene | Isobornyl methacrylate | Camphene dimer | Isoborneol |
| 2 | 1 | 10.9 | 21.3 | 61.3 | 4.6 | 0.5 |
| 3 | 2 | 10.8 | 22.1 | 61.4 | 3.9 | 0.6 |
| 4 | 3 | 10.9 | 22.5 | 61.9 | 3.2 | 0.5 |
| 5 | 4 | 10.8 | 23.1 | 61.8 | 2.8 | 0.4 |
| 6 | 5 | 11.2 | 25.0 | 60.3 | 2.0 | 0.2 |
| 7 | 6 | 11.0 | 24.1 | 61.3 | 2.1 | 0.4 |

As can be seen from Tab. 1, the reuse of the catalyst brings no disadvantages; surprisingly, the composition improves in respect of the nonrecyclable by-products.

EXAMPLE 8

66.3 g (0.77 mol) of methacrylic acid, 92.4 g (0.70 mol) of dicyclopentadiene, 0.078 g of hydroquinone monomethyl ether as polymerization inhibitor and 17 g of montmorillonite K10 (Südchemie) are weighed into a 500 ml four-neck round-bottom flask containing a sickle stirrer with stirrer sleeve, thermometer, reflux condenser, air inlet tube and temperature-regulated oil bath. While stirring and passing in air, the mixture is heated at 90° C. for 6 hours. The mixture is allowed to cool, the montmorillonite is filtered off and the filtrate is analysed by gas chromatography. The catalyst can optionally be reused. GC analysis indicates 11% of unreacted methacrylic acid, 22% of unreacted dicyclopentadiene, 60% of dicyclopentenyl methacrylate isomer mixture and a total 6% of dicyclopentadiene oligomers and 0.6% of bis(dicyclopentenyl) ether.

The invention claimed is:

1. A process for preparing bicyclic or tricyclic (meth)acrylates, comprising by reacting (meth)acrylic acid with a bicyclic or tricyclic hydrocarbon which contains at least one double bond in the presence of a montmorillonite catalyst.

2. The process according to claim 1, wherein the montmorillonite catalyst is present in an amount of 5-50 % by weight, based on (meth)acrylic acid.

3. The process according to claim 1, wherein the bicyclic hydrocarbon is camphene, norbornene or dicyclopentadiene.

4. The process according to claim 1, wherein the catalyst is bentonite.

5. The process according to claim 1, wherein the reaction is carried out at 50-250° C.

* * * * *